(12) United States Patent
Mikami et al.

(10) Patent No.: US 8,299,273 B2
(45) Date of Patent: Oct. 30, 2012

(54) BIPHENYLTETRACARBOXYLIC ACID DIANHYDRIDE AND PROCESS FOR PRODUCING THE SAME, AND POLYIMIDE FORMED FROM THE SAME AND PROCESS FOR PRODUCING THE SAME

(75) Inventors: Hiroshi Mikami, Kitakyushu (JP); Makoto Nitta, Kitakyushu (JP); Naoki Noguchi, Kitakyushu (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 12/855,597

(22) Filed: Aug. 12, 2010

(65) Prior Publication Data

US 2010/0305299 A1 Dec. 2, 2010

Related U.S. Application Data

(62) Division of application No. 11/570,812, filed as application No. PCT/JP2005/011812 on Jun. 28, 2005, now Pat. No. 7,842,824.

(30) Foreign Application Priority Data

Jun. 28, 2004 (JP) ................. 2004-189465

(51) Int. Cl.
C07D 307/89 (2006.01)
(52) U.S. Cl. ...................................... 549/241
(58) Field of Classification Search ............. 549/241
See application file for complete search history.

(56) References Cited

U.S. PATENT DOCUMENTS

| | | | |
|---|---|---|---|
| 4,684,738 A | 8/1987 | Fujiwara et al. |
| 4,958,002 A | 9/1990 | Imatani et al. |
| 6,329,494 B1 | 12/2001 | Arai et al. |
| 6,600,053 B2 | 7/2003 | Arai et al. |
| 2002/0037991 A1 | 3/2002 | Arai et al. |

FOREIGN PATENT DOCUMENTS

| | | |
|---|---|---|
| JP | 48-44432 | 12/1973 |
| JP | 57 15098 | 3/1982 |
| JP | 58-117954 | 7/1983 |
| JP | 61-249977 | 11/1986 |
| JP | 62-30773 A | 2/1987 |
| JP | 1-104063 | 4/1989 |
| JP | 1-299282 | 12/1989 |
| JP | 3-123756 A | 5/1991 |
| JP | 4-82859 A | 3/1992 |
| JP | 4 37078 | 6/1992 |
| JP | 7-62013 | 7/1995 |
| JP | 7-206763 A | 8/1995 |
| JP | 8-134056 | 5/1996 |
| JP | 8-134056 A | 5/1996 |
| JP | 8-134057 A | 5/1996 |
| JP | 8 143480 | 6/1996 |
| JP | 2000-281671 | 10/2000 |
| JP | 2003 335768 | 11/2003 |
| JP | 2003-335768 A | 11/2003 |
| JP | 2004-150641 | 5/2004 |

OTHER PUBLICATIONS

Japanese Office Action issued on Aug. 2, 2011 in corresponding Japanese Application No. 2005-187065 (with an English Translation).
Perry et al., Chemical Engineer's Handbook, (1973) McGraw-Hill, p. 19-19 to 19-26.
Hergenrother, Polymer 43 (2002) pp. 5077-5093.
Office Action issued Jul. 22, 2010, in Korean Patent Application No. 2006-7027358 (English translation only).
Office Action issued Feb. 14, 2012, in Japanese Patent Application No. 2005-187065 (submitting English translation only, Japanese Office Action previously filed on Apr. 27, 2012).
Japanese Information Statement issued Jan. 31, 2012, in Patent Application No. 2005-187065 (with English-language translation).
Japanese Office Action issued Feb. 14, 2012, in Patent Application No. 2005-187065.

*Primary Examiner* — Bernard Dentz
(74) *Attorney, Agent, or Firm* — Oblon, Spivak, McClelland, Maier & Neustadt, L.L.P.

(57) ABSTRACT

To provide a process for producing BPDA whereby high productivity is attained while high purity is maintained.
A process for producing biphenyltetracarboxylic acid dianhydride, which comprises heating biphenyltetracarboxylic acid to produce biphenyltetracarboxylic acid dianhydride, characterized in that the heating is carried out at a pressure of from $1 \times 10^2$ Pa to $1.1 \times 10^5$ Pa to a maximum temperature in a range of from 210° C. to 250° C. in such a manner that the temperature rising rate is higher than 50° C./hr for a period of at least ¼ of the time for the temperature rise from 60° C. to 210° C., and the temperature is maintained to be from 150° C. to 250° C. for from 0.5 to 10 hours.

9 Claims, 3 Drawing Sheets

BIPHENYLTETRACARBOXYLIC ACID DIANHYDRIDE AND PROCESS FOR PRODUCING THE SAME, AND POLYIMIDE FORMED FROM THE SAME AND PROCESS FOR PRODUCING THE SAME

TECHNICAL FIELD

The present invention relates to biphenyltetracarboxylic acid dianhydride (hereinafter referred to as BPDA) and a process for producing the same, and a polyimide formed from the same and a process for producing the same.

BACKGROUND ART

BPDA is a compound useful as a starting material for the production of an aromatic polyimide which is now attracting attention as a heat resistant resin. An aromatic polyimide formed from BPDA can be prepared by either a process for producing it by a polymerization reaction of BPDA and an aromatic diamine or a process for ring-closing imidation of a polyamic acid obtained by polymerization of BPDA and an aromatic diamine at a low temperature in the vicinity of room temperature.

BPDA can be obtained by heating biphenyltetracarboxylic acid (hereinafter referred to as BTC) in a nitrogen atmosphere under a pressure of from atmospheric pressure to a reduced pressure of 40 mmHg at from 100 to 500° C. for a dehydration ring-closing reaction (JP-B-57-15098). However, as a result of a study on a problem that the viscosity cannot sufficiently be increased when it is formed into an aromatic polyimide, it has been found that the cause may be biphenyltricarboxylic acid and/or its anhydride (hereinafter referred to as the "tri-derivative" included in the product. As a means to solve such a problem, a process for obtaining BPDA has been proposed wherein the content of the tri-derivative is reduced to a level of less than 0.2 wt % by carrying out the heating of BTC under specific conditions (U.S. Pat. No. 4,958,002).

Namely, this proposal is characterized in that when BPDA is formed by heating BTC crystals in an atmosphere of an inert gas at a dehydrating temperature of at least 250° C. to form an anhydride, preheating for temperature rise from 80° C. to the dehydrating temperature, is carried out so that the average temperature-rising rate will not be higher than 50° C./hr. In such a manner, water attached to the crystal and crystal water are removed and then the preheated crystals are heated at a dehydration temperature of from 250 to 300° C. for at least three hours for dehydration. Further, in order to realize the heating under the above-mentioned specific conditions, this proposal also proposes to employ a reaction tank (drying machine) which houses a disk-type stirring device having rotary vanes on a horizontal rotary shaft having a hollow portion internally formed to let pressurized steam or a heat resistant heating medium flow therethrough, and which has an outer wall substantially covered by a jacket to let pressurized steam or a heat resistant heating medium flow therethrough.

However, as is evident from Examples in U.S. Pat. No. 4,958,002, it takes a long time exceeding 9 hours even only for the time required for the preheating, although BPDA of high purity with a tri-derivative content of from 0.06 to 0.07 wt % is obtained. If the time required for the dehydration ring-closing reaction is further added, the process requires a long time, and a solution is desired to increase the productivity of the process while the high purity is maintained.

DISCLOSURE OF THE INVENTION

Object to be Solved by the Invention

In view of the above demand, it is an object of the present invention to provide a process for producing BPDA whereby the productivity of the process can be improved while the high purity is maintained, BPDA, and a polyimide formed from the same and a process for producing the polyimide.

Means to Accomplish the Object

The present inventors have found it possible to attain the high purity while the high productivity is maintained and to suppress coloration of BPDA, by a dehydration reaction under prescribed heating conditions. Further, they have found that the high purity can be attained while the high productivity is maintained by using for the heating and dehydration reaction a heating device having groups of hollow rotary heating members having a prescribed shape properly disposed and secured to a hollow rotary shaft. On the basis of such discoveries, the present invention has been accomplished.

The present invention provides a process for producing biphenyltetracarboxylic acid dianhydride, which comprises heating biphenyltetracarboxylic acid to produce biphenyltetracarboxylic acid dianhydride, characterized in that the heating is carried out at a pressure of from $1\times10^2$ Pa to $1.1\times10^5$ Pa to a maximum temperature in a range of from 210° C. to 250° C. in such a manner that the temperature-rising rate is higher than 50° C./hr for a period of at least ¼ of the time for the temperature rise from 60° C. to 210° C., and the temperature is maintained to be from 150° C. to 250° C. for from 0.5 to 10 hours.

Usually, biphenyltetracarboxylic acid dianhydride (BPDA) is a compound name, but in the present invention, in order to simplify the representation, also crystals composed substantially of biphenyltetracarboxylic acid dianhydride and containing a very small amount of other substances, may simply be referred to as biphenyltetracarboxylic acid dianhydride (BPDA).

Further, in a case where regions wherein the temperature-rising rate is higher than 50° C./hr are discontinuously present, their total time may be at least ¼ of the time for the temperature rise from 60° C. to 210° C.

For the heating, the following heating device is preferably employed. Namely, it is a heating device which houses a hollow rotary shaft provided with a plurality of hollow rotary heating members and which is designed to feed a heated heating medium to hollow portions of the rotary heating members via a hollow portion of the rotary shaft, and also to a heating jacket provided as the case requires, thereby to supply an amount of heat required for the reaction by heat transfer from each surface of such a rotary shaft, rotary heating members, and, if required, a heating jacket, wherein each of the hollow rotary heating members has a wedge shape as viewed from the side and a fan shape as viewed from the front and is secured at the neck portion of the fan shape to the hollow rotary shaft, and yet, from one end of the heating device, a biphenyltetracarboxylic acid powder as a starting material is continuously supplied, and the powder is heated as it is contacted with the hollow rotary heating members which are rotating and is subjected to a dehydration reaction while it is transferred in an axial direction in the heating device, and biphenyltetracarboxylic acid dianhydride as a product is continuously discharged from the other end of the heating device.

Preferably, in the heating device, at least two such hollow rotary shafts are provided in a horizontal direction in parallel to one another; on each rotary shaft, rotary heating members disposed at two positions symmetrical about a point, as viewed from the front, are provided alternately in the axial direction in a predetermined number at equal distances; and the groups of rotary heating members provided on the adjacent rotary shafts take such spatial disposition that they are mutually free from contact with each other during rotation of both rotary shafts.

More preferably, the heating device is provided with a heating jacket.

In the present invention, the heating is preferably followed by sublimation purification, and the temperature for the sublimation purification is preferably at least 250° C. Here, in a case where the sublimation purification is carried out at a temperature of at least 250° C., the treatment up to 250° C. may be regarded as the heating, and the treatment at 250° C. or higher may be regarded as the sublimation purification.

And, the biphenyltetracarboxilic acid dianhydride obtained by the sublimation purification is preferably such that a solution obtained by dissolving it at a concentration of 0.05 g/ml in a 2N NaOH aqueous solution has a transmittance of light with a wavelength of 400 nm being at least 90%. Preferably, such a transmittance of light is at least 98%. Further preferably, its palladium content is not higher than 0.2 mass ppm. Particularly preferably, the total content of biphenyltricarboxylic acid (tri-derivative) and its anhydride, and biphenyltetracarboxylic acid monoanhydride (half-derivative) is not more than 0.3 mass %.

Further, the conversion of BTC to BPDA is preferably at least 99%.

In another aspect, the present invention provides a process for producing biphenyltetracarboxylic acid dianhydride, which comprises heating biphenyltetracarboxylic acid to produce biphenyltetracarboxylic acid dianhydride, characterized in that the heating is carried out by means of a heating device which houses a hollow rotary shaft provided with a plurality of hollow rotary heating members and which is designed to feed a heated heating medium to hollow portions of the rotary heating members via a hollow portion of the rotary shaft, and also to a heating jacket provided as the case requires, thereby to supply an amount of heat required for the reaction by heat transfer from each surface of such a rotary shaft, rotary heating members, and, if required, a heating jacket, wherein each of the hollow rotary heating members has a wedge shape as viewed from the side and a fan shape as viewed from the front and is secured at the neck portion of the fan shape to the hollow rotary shaft, and yet, from one end of the heating device, a biphenyltetracarboxylic acid powder as a starting material is continuously supplied, and the powder is heated as it is contacted with the hollow rotary heating members which are rotating and is subjected to a dehydration reaction while it is transferred in an axial direction in the heating device, and biphenyltetracarboxylic acid dianhydride as a product is continuously discharged from the other end of the heating device.

Preferably, in the heating device, at least two such hollow rotary shafts are provided in a horizontal direction in parallel to one another; on each rotary shaft, rotary heating members disposed at two positions symmetrical about a point, as viewed from the front, are provided alternately in the axial direction in a predetermined number at equal distances; and the groups of rotary heating members provided on the adjacent rotary shafts take such spatial disposition that they are mutually free from contact with each other during rotation of both rotary shafts. More preferably, the heating device is provided with a heating jacket.

In another aspect, the present invention provides a biphenyltetracarboxylic acid dianhydride characterized in that a solution obtained by dissolving it at a concentration of 0.05 g/ml in a 2N NaOH aqueous solution has a transmittance of light with a wavelength of 400 nm being at least 98%. Preferably, its palladium content is not higher than 0.2 mass ppm. More preferably, the total content of biphenyltricarboxylic acid (tri-derivative) and its anhydride, and biphenyltetracarboxylic acid monoanhydride (half-derivative) is not more than 0.3 mass %.

Preferably, this biphenyltetracarboxylic acid dianhydride is obtained by heating and sublimation purification of biphenyltetracarboxylic acid, and the heating is carried out at a pressure of from $1 \times 10^2$ Pa to $1.1 \times 10^5$ Pa to a maximum temperature in a range of from 210° C. to 250° C. in such a manner that the temperature-rising rate is higher than 50° C./hr for a period of at least ¼ of the time for the temperature rise from 60° C. to 210° C., and the temperature is maintained to be from 150° C. to 250° C. for from 0.5 to 10 hours.

In still another aspect, the present invention provides a process for producing a polyimide, characterized by reacting the biphenyltetracarboxylic acid dianhydride obtained by the process as described above and an aromatic diamine. Preferably, this polyimide has, when formed into a film having a thickness of 11 μm, a transmittance of light with a wavelength of 400 nm being at least 20%, more preferably at least 25%, further preferably at least 30%.

In still another aspect, the present invention provides a polyimide characterized in that it is obtained by reacting the biphenyltetracarboxylic acid dianhydride as defined above and an aromatic diamine. Preferably, this polyimide has, when formed into a film having a thickness of 11 μm, a transmittance of light with a wavelength of 400 nm being at least 20%, more preferably at least 25%, further preferably at least 30%.

Effects of the Invention

In the present invention, the heating conditions are adjusted to be within the specific ranges, or the specific device is sophisticatedly used for the heating and dehydration reaction of BTC powder as the starting material, whereby remarkable effects can be obtained such that high productivity can be attained while the high purity of BPDA product is maintained. Further, there is an affect such that coloration of BPDA can be suppressed. Further, there is an effect such that it is possible to produce a polyimide having a high degree of polymerization with excellent heat resistance and a small degree of coloration. In the present invention, it is not necessary to have all of such effects provided, and it is sufficient that at least one of them is provided.

MEANINGS OF SYMBOLS

1: heating device
2: hollow rotary heating member
3: hollow rotary shaft
5: heating jacket

20: hollow portion of a hollow rotary heating member
21: fan-shaped outer surface of a hollow rotary heating member
22: subsidiary scraping surface of a hollow rotary heating member
23: inlet for a heating medium to a hollow rotary heating member
24: outlet for a heating medium from a hollow rotary heating member
30: hollow portion of the hollow rotary shaft
31: inlet for a heating medium to the hollow rotary shaft
32: outlet for a heating medium from the hollow rotary shaft
41: inlet for starting material powder
42: outlet for product powder
51: inlet for a heating medium to the heating jacket
52: outlet for a heating medium from the heating jacket
61: inlet for an inert gas medium
62: outlet for an inert gas medium

BEST MODE FOR CARRYING OUT THE INVENTION

Now, the present invention will be described in detail.

Biphenyltetracarboxylic acid as the starting material of the present invention can be prepared usually hydrolyzing tetramethyl biphenyltetracarboxylate obtained by a dehydration dimerization reaction of dimethyl o-phthalate, in an aqueous medium in the presence of an acid catalyst. Otherwise, it can be prepared by subjecting 4-phthalic acid obtainable by halogenation of phthalic anhydride, to a dehalogenation dimerization reaction in an aqueous medium in the presence of an alkali/reducing agent/Pd catalyst to obtain a tetraalkali metal biphenyltetracarboxylate, and neutralizing it with a mineral acid. Biphenyltetracarboxylic acid thus prepared is substantially entirely 3,4,3',4'-isomer.

BTC produced by such a method is subjected to a dehydration reaction by a suitable method such as a method of heating in the absence of a solvent under reduced pressure or a method of heating in a liquid medium which does not substantially dissolve BTC, such as acetic anhydride, to produce BPDA. Here, the production route of BTDA by the latter method and an aromatic polyimide resin may be shown by chemical formulae as follows.

The biphenyltetracarboxylic acid obtained by the above method preferably has a content of useful fine particles with a size of from 5 to 30 μm being not more than $7 \times 10^4$ particles per 1 g, and usually, biphenyltetracarboxylic acid containing from $5 \times 10^3$ to $7 \times 10^4$ particles per 1 g is used. For this purpose, a liquid material and a solvent to be used for the above preparation are preferably filtered to remove insoluble fine particles. Further, a reaction solution having a solid catalyst, etc. removed is also preferably filtered in the same manner for adjustment so that the content of insoluble fine particles will be not more than $7 \times 10^4$ particles per 1 g. The filter to be used in such a case may vary depending upon the conditions. However, for example, a filter with a perforation diameter of 1 μm may be used alone, or a plurality of such filters may be used in combination in series.

Heating

In the present invention, the heating is carried out by maintaining starting material biphenyltetracarboxylic acid under a pressure within a range of from $1 \times 10^2$ Pa to $1.1 \times 10^5$ Pa at a temperature of from 150 to 250° C. usually for from 0.5 hour to 10 hours. At that time, the maximum temperature in the heating is within a range of from 210° C. to 250° C., and the temperature-rising rate is higher than 50° C./hr for a period of at least ¼ of the time for the temperature rise from 60° C. to 210° C.

Heretofore, it was common to carry out dehydration by heating at a dehydration temperature of from 250 to 300° C. for at least three hours, and as heated at a high temperature for a long period of time, BPDA was likely to be modified and undergo coloration. The present inventors have found that dehydration of BTC is possible even by heating at a temperature of not higher than 250° C. by selecting the conditions. Yet, the temperature-rising rate can be made higher than ever, and the heating can be completed in a short time. Therefore, coloration of BPDA can be suppressed, and it is possible to obtain BPDA having a high light transmittance and an extremely small degree of coloration.

In the present invention, starting material biphenyltetracarboxylic acid may be one in a state wet with water. In such a case, during the temperature-rise, the attached water as well as crystal water will be removed by evaporation, followed by a dehydration ring-closing reaction. Such a series of reactions are preferably carried out under atmospheric pressure while an inert gas is circulated or under reduced pressure, since the reaction rate can be improved when the attached water, crystal water and water formed by the dehydration ring-closing reaction are purged out of the reaction system. The time required for the dehydration ring-closing reaction varies depending upon the heating rate, the heating temperature, the vacuum degree, the presence or absence of the attached water, etc., but may usually be selected within a range of from 0.5 to 10 hours.

In the heating of the present invention, the pressure range is from $1 \times 10^2$ to $1.1 \times 10^5$ Pa. If the pressure is too high, the dehydration reaction tends to hardly proceed, and if the pressure is too low, the cost for maintaining the reduced pressure state becomes high. The pressure range is preferably from $1 \times 10^2$ to $1 \times 10^5$ Pa.

The maximum temperature is within a range of from 210° C. to 250° C., more preferably from 220° C. to 250° C., further preferably from 225° C. to 250° C. If it is too low, the dehydration reaction tends to hardly proceed, but if it exceeds 250° C., BTC or BPDA will be modified by the heat and undergo coloration. It is preferably at most 248° C.

In the heating of the present invention, the temperature-rising rate is higher than 50° C./hr (50° C. per one hour) for a period of at least ¼ of the time for the temperature rise of from 60° C. to 210° C. (hereinafter referred to simply as the temperature-rising time). Here, during the temperature-rising time, the temperature-rising rate may optionally be changed. If regions where the temperature-rising rate is higher than 50° C./hr, are discontinuously present, their total time may be at least ¼ of the temperature-rising time. As the total time of such regions is long, the temperature will be raised quickly, whereby the time for BTC or BPDA to be exposed to the heat, may be shortened, and coloration by modification may be suppressed. Further, it is thereby possible to shorten the production time or to save the heat source. Preferably, the temperature-rising rate is made higher than 50° C./hr for a period of at least ⅓ of the temperature-rising time. The temperature-rising rate may be made higher than 50° C./hr over the entire temperature-rising time.

More preferably, the temperature-rising rate is higher than 60° C./hr for a period of at least ¼ of the temperature-rising time, and further preferably, the temperature-rising rate is higher than 70° C./hr for a period of at least ¼ of the temperature-rising time. If the temperature-rising rate is too high, a temperature distribution is likely to result in the interior, whereby the heating tends to be non-uniform, and the dehydration reaction tends to be non-uniform. Accordingly, it is usually at most 400° C./hr, preferably at most 300° C./hr, further preferably at most 250° C./hr.

Further, the average temperature-rising rate over the entire temperature-rising time from 60° C. to 210° C. is preferably higher than 50° C./hr.

In the heating of the present invention, the temperature is maintained to be from 150° C. to 250° C. for from 0.5 hour to 10 hours including not only the time for the temperature-rise but also the time for constant temperature and temperature drop. Namely, when BTC is heated for conversion to BPDA, the time for maintaining it at a temperature of from 150° C. to 250° C. is at least 0.5 hour and at most 10 hours. If the time is too long, deterioration of BTC or BPDA by the heat tends to proceed. However, if it is too short, the dehydration reaction is likely to be inadequate. It is preferably at least one hour, more preferably at least two hours, further preferably at least 3 hours.

Preferably, the conversion of BTC to BPDA is at least 99%.

Heating Device

Now, the heating device which is preferably used in the present invention, will be described with reference to the drawings.

Figure 1:
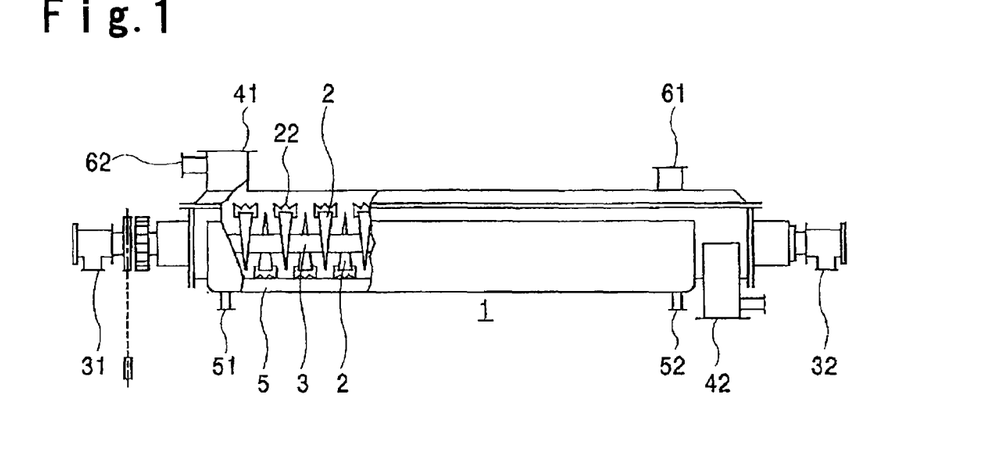
FIG. 1 is a partly cut out side view of the heating device.
Figure 2:
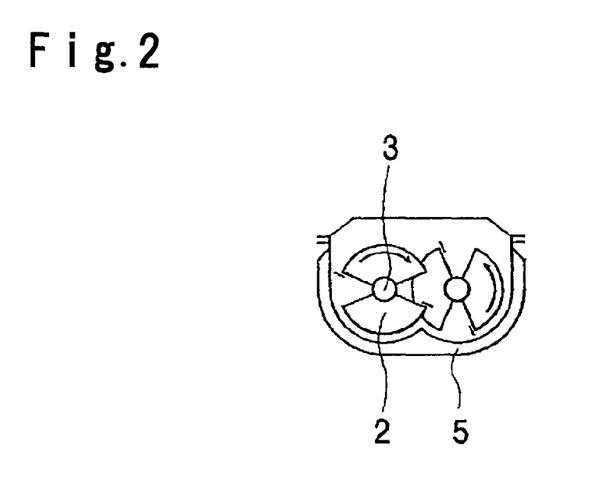
FIG. 2 is a schematic vertically cross-sectional front view of the cut out portion.
Figure 3:
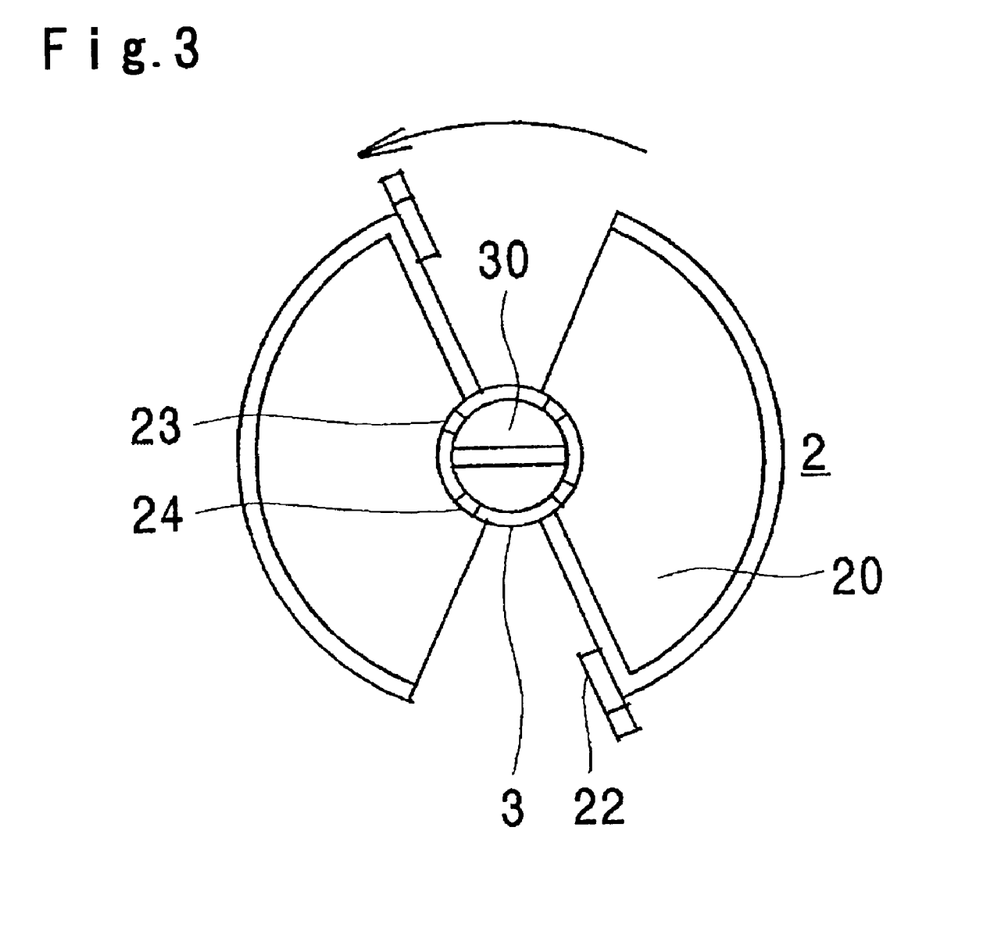
FIG. 3 is a partial enlarged view of FIG. 2 showing the hollow rotary heating members and the hollow rotary shaft.
Figure 4:
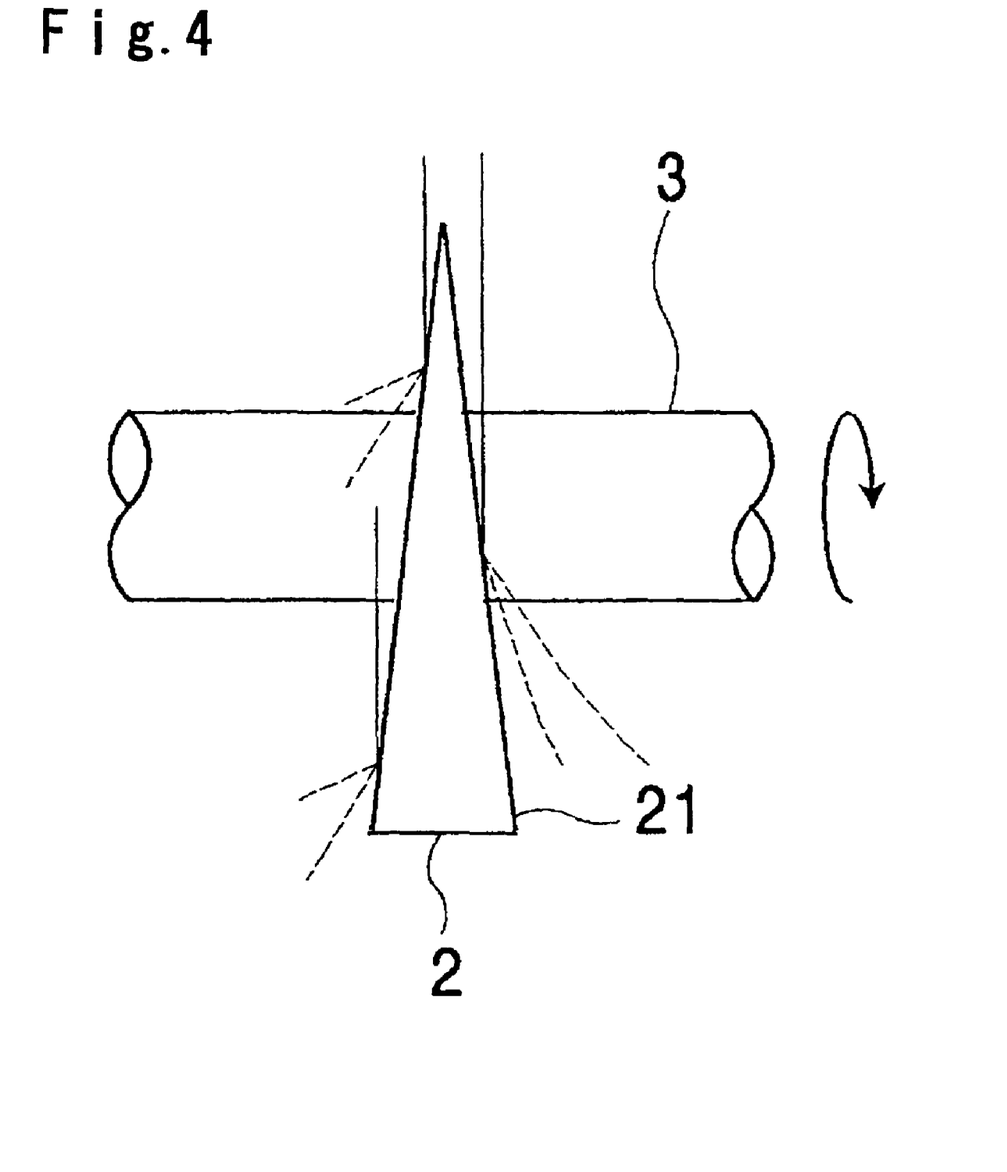
FIG. 4 is a schematic view illustrating a mutual motion of the powder to be heated to the surface of a hollow rotary heating member.

FIG. 1 is a partly cut out side view of the heating device which is preferably used in the practice of the present invention. FIG. 2 is a schematic vertically cross-sectional front view of the cut out portion; FIG. 3 is a partial enlarged view of FIG. 2 showing hollow rotary heating members and a hollow rotary shaft; and FIG. 4 is a schematic view illustrating a mutual motion of the powder to be heated to the surface of a hollow rotary heating member.

In the Figs., 1 represents the heating device, 2 a hollow rotary heating member, 3 a hollow rotary shaft, 5 a heating jacket, 20 the hollow portion of a hollow rotary heating member, 21 the fan-shaped outer surface of a hollow rotary heating member, 22 a subsidiary scraping surface of a hollow rotary heating member, 23 an inlet for a heating medium to a hollow rotary heating member, 24 an outlet for the heating medium from the hollow rotary heating member, 30 a hollow portion of the hollow rotary shaft, 31 an inlet for a heating medium to the hollow rotary shaft, 32 an outlet for the heating medium from the hollow rotary shaft, 41 an inlet for starting material powder, 42 an outlet for the product powder, 51 an inlet for a heating medium to a heating jacket, 32 an outlet for the heating medium from the heating jacket, 61 an inlet for an inert gas medium, and 62 an outlet for the inert gas medium.

The production of biphenyltetracarboxylic acid dianhydride (BPDA) by carrying out the heating of biphenyltetracarboxylic acid (BTC), followed by a dehydration reaction, by means of this device, is carried out as follows. Firstly, starting material BTC powder is supplied from the inlet (41) to the heating device (1) as shown in FIG. 1. As shown in the cut out portion in the same Fig., or as shown also in FIG. 2, hollow rotary shafts (3) each provided with a plurality of hollow rotary heating members (2) are installed in this heating device (1). Each hollow rotary heating member (2) has substantially a fan shape as viewed from the front as shown in FIGS. 2 and 3 and is secured at the neck portion of the fan shape to the hollow rotary shaft (3). However, this heating member (2) is a three dimensional body having a wedge form as viewed from the side as shown in FIGS. 1 and 4. Further, in the heating device (1) shown in FIGS. 1 and 2, two hollow rotary shafts (3) are provided in parallel in a horizontal direction, and on each rotary shaft (3), rotary heating members (2) disposed at two positions symmetrical about a point, as viewed from the front, are provided alternately in the axial direction in a predetermined number at equal distances. Such a shape and disposition of the rotary heating members (2) are considered to promote the motion of the powder in the vicinity of the heat transfer surface and to be effective to increase the heat transfer coefficient. Further, the groups of rotary heating members (2) provided on the adjacent rotary shafts (3) take such spatial disposition that they are mutually free from contact with each other during rotation of both rotary shafts.

Thus, when a power is given to the hollow rotary shafts (3) in such a heating device (1) to rotate the rotary shafts and many hollow rotary heating members (2) secured thereto, the BTC powder continuously supplied to the inlet (41) for the starting material located at one end of the heating device will be moved up and down in the space in the device. Not only that, as shown in FIG. 4, by the contact with the surface (21) of the rotating rotary heating members, the powder is sequentially advanced in the space, and by the heat transfer from the surface of the rotary shafts (3), the rotary heating members (2) and the heating jacket (5) during the period of time, the dehydration reaction will be completed, whereupon from the outlet (42), a powder of product BDPA will be continuously discharged. On the other hand, steam evaporated during the drying and dehydration reaction will be discharged from the outlet (62) as accompanied by an inert gas medium during the time when the inert gas medium introduced from the inlet (61) flows in the upper space of the powder heated and stirred.

Here, the heating medium to supply heat to the fan-shaped surface (21) of the rotary heating member to carry out heat transfer in contact with the powder, is supplied from the inlet (31) to the hollow rotary shafts (3) of the heating device, in the case shown in FIG. 1. From the hollow portion (30) of the rotary shaft to the hollow rotary heating members (2), in the case shown in FIG. 3, the heating medium will be introduced via the inlet (23) formed in each heating member and will be discharged via the outlet (24) formed in each heating member and will be returned to the hollow portion (30) of the hollow rotary shaft. FIG. 3 illustrates a case wherein a partition wall is provided in the hollow portion (30) of the rotary shaft to divide a pathway for a heating medium to be supplied afresh from a pathway for the heating medium to be returned.

With respect to such a heating device, many types are commercially available, for example, by product names such as a paddle dryer, a single paddle dryer and a multi fin processor from NARA MACHINERY CO., LTD., and it is possible to select the number of hollow rotary shafts, the rotational speed, the number of hollow rotary heating members, the heat transfer area, etc. Further, it is thereby easy to control the temperature and the retention time for the dehydration reaction.

With the heating device of the present invention, it has been found possible to accomplish high productivity while the high purity is maintained, as a result of using the heating device wherein the groups of hollow rotary heating members having the specific shape are properly disposed and secured to the hollow rotary shafts, in the heating and dehydration reaction of starting material BTC powder.

Sublimation Purification

The biphenyltetracarboxylic acid dianhydride obtainable by the above-described heating of BTC is one having a sufficiently high purity, as the light transmittance is high, the degree of coloration is low, the Pd content is small, the residual amount of unreacted BTC is extremely small, and the amount of the half-derivative or the tri-derivative formed by the side reaction is extremely small. However, when it is further heated and evaporated, and the evaporated biphenyltetracarboxylic acid dianhydride is cooled (sublimation purification step), high purity biphenyltetracarboxylic acid dianhydride wherein the Pd content and the content of insoluble fine particles are extremely small, can be precipitated as crystals and thus can easily be recovered. This evaporation operation is preferably carried out by heating under reduced pressure. If the heating temperature is too low, it tends to be difficult to efficiently evaporate the biphenyltetracarboxylic acid dianhydride, and if it is too high, the biphenyltetracarboxylic acid dianhydride is likely to undergo heat deposition, such being undesirable. Preferably, the temperature is at least 250° C., more preferably at least 300° C. However, it is preferably at most 400° C., more preferably at most 350° C. Further, the pressure is preferably a reduced pressure of at most 4,000 Pa, preferably a reduced pressure of at most 2,700 Pa.

In a case where the heating and the sublimation purification are carried out continuously, and the sublimation purification is carried out at a temperature of at least 250° C., the treatment up to 250° C. may be regarded as the heating, and the treatment of at least 250° C. may be regarded as the sublimation purification.

BPDA

BPDA of the present invention is such that a solution obtained by dissolving it in a state after the above-mentioned sublimation purification at a concentration of 0.05 g/ml in a 2N NaOH aqueous solution has a transmittance of light with a wavelength of 400 nm being at least 90%, and thus, it is excellent as a starting material for the production of a polyimide. Preferably, the light transmittance is at least 98%. A polyimide has excellent characteristics such as high heat resistance, low dielectric constant, high dimensional stability, high mechanical strength and chemical resistance and thus is used in various applications in the field related to microelectronics, and its application to optical uses such as alignment films for liquid displays, optical waveguides or optical components, is being studied.

However, during the production of a polyimide, it was exposed to a high temperature, and heretofore, coloration to a slightly yellow type was unavoidable, which used to be a factor to hinder an application to optical uses.

By a study by the present inventors, coloration of BPDA as the starting material has been found as one of the causes for the coloration of the polyimide. Namely, it is possible to suppress coloration of a polyimide by using, as starting material, BPDA, of which a solution obtained by dissolving it at a concentration of 0.05 g/ml in a 2N NaOH aqueous solution, has a transmittance of light with a wavelength of 400 nm being at least 90%. Preferably, BPDA having a light transmittance of at least 98%, is employed.

Heretofore, a few methods have been proposed for purification of BPDA. For example, as a purification method for BPDA, JP-B-4-37078 discloses a method wherein BTC is heated at a temperature of from 150 to 230° C. under reduced pressure for a dehydration reaction, then formed BPDA is continuously heated and evaporated at a temperature of from 250 to 400° C. under a reduced pressure of not higher then 30 mmHg, and then, the vapor of evaporated BPDA is cooled for recovery in the form of purified crystals. Or JP-A-8-143480 discloses a method wherein at the time of purifying a high melting point organic compound by melting and evaporating the high melting point organic compound, followed by cooling, the linear velocity of the vapor during the evaporation of the high melting point organic compound, is controlled to reduce the amount of insoluble fine particles contained in the high melting point organic compound. However, even by these methods, reduction of the coloration of BPDA was inadequate.

Whereas, the present inventors have found that BPDA obtained by carrying out conversion of BTC to BPDA by heating under the above-mentioned specific conditions, followed by sublimation purification, has very high purity, little coloration and high transparency. However, the method to obtain BPDA having high transparency, of the present invention, is not limited thereto.

BPDA of the present invention has a palladium content of not higher than 0.2 mass ppm, in the state after the above-mentioned sublimation purification. Palladium is usually used as a catalyst at the time of producing BTC, and a very small amount of palladium is usually obliged to remain in BPDA. However, it has been found that if palladium is contained in BPDA or in the polyimide, BPDA or the polyimide tends to be gradually decomposed by its catalytic action, and such palladium tends to be a factor to cause coloration with time.

Further, in a case where the polyimide is used as a material for a precise electronic circuit board, if a metal element such as palladium is contained, it may adversely affect the characteristics of the electronic circuit, such being undesirable.

Therefore, BPDA of the present invention preferably has a palladium content of not higher than 0.2 mass ppm, more preferably not higher than 0.1 mass ppm, further preferably not higher than 0.05 mass ppm. The smaller the palladium content the better. However, it is difficult to completely remove it, and the content is usually at least 0.05 mass ppb.

The method to reduce the palladium content is not particularly limited, but, for example, the above-mentioned sublimation purification may be employed.

In the BPDA of the present invention, the total content of biphenyltricarboxylic acid and its anhydride (generally referred to as a tri-derivative), and biphenyltetracarboxylic acid monoanhydride (a half-derivative) is not more than 0.3 mass %. Further preferably, the conversion of BTC to BPDA is at least 99%. A polyimide usually shows excellent heat resistance and mechanical strength, as the polymerization degree is high. As a result of a study made by the present inventors, it has been found that when one having a high purity is used for BPDA as starting material, it is possible to obtain a polyimide having a high polymerization degree. Accordingly, BPDA having a small content of the tri-derivative or the half-derivate and having little residual amount of BTC can be used suitably as starting material for the polyimide.

Polyimide

By reacting BPDA of the present invention with an aromatic diamine, it is possible to obtain a polyimide having excellent characteristics.

A polyimide usually shows excellent heat resistance and mechanical strength as the polymerization degree is high. By a study made by the present inventors, it has been found that when one having a high purity is used for BPDA as starting material, it is possible to obtain a polyimide having a high polymerization degree. Further, a polyimide resin is frequently used as a material for a precise electronic circuit board in view of the characteristics such as high heat resistance and high dimensional stability, and it is preferred to use one having a small content of impurities, particularly metals, for BPDA as starting material. Further, it has been found that by using one having high transparency with little coloration for BPDA as starting material, it is possible to obtain a polyimide excellent in transparency with little coloration of slightly yellow type.

Accordingly, by reacting BPDA of the present invention having a high purity, a small Pd content and high transparency, with a diamine, it is possible to obtain a polyimide having a high polymerization degree, excellent mechanical strength, a small metal content and excellent transparency with little coloration of slightly yellow type.

And, also in a case where the obtained polyimide is made into a film, a surface roughness will be small, and the processability of the film will be excellent. Preferably, the obtained polyimide is such that when it is formed into a film having a thickness of 11 μm, the transmittance of light with a wavelength of 400 nm is at least 20%, more preferably at least 25%, further preferably at least 30%. The higher the light transmittance, the better, but it is usually at most about 90%.

The diamine component to be reacted with BPDA is not particularly limited, and a known aromatic diamine component may be mentioned such as diaminodiphenyl ether, p-phenylenediamine, bisaminophenoxyphenylpropane or o-tolidine. Two or more of them may be used in combination. The amount of the diamine component to BPDA is not particularly limited, but usually, BPDA and the diamine component are reacted in about equal molar amounts. Here, as the diamine component, it is also preferred to employ one having little coloration. BPDA and the diamine component are reacted in an organic solvent to firstly produce a polyamic acid. The organic solvent to be used is not particularly limited. Usually, one capable of dissolving the diamine component is preferably employed such as N-methylpyrrolidone, dimethylacetoamide, dimethylformamide or dimethylsulfoxide. The reaction temperature is usually from 0 to 50° C. Further, the reaction time is usually from about 1 to 50 hours.

The polyamic acid solution thus obtained may be imidated by various methods depending upon the particular application. The method is not particularly limited. For example, an imidation method may be employed wherein a polyamic acid solution is heated as it is at a temperature of from 100 to 500° C. for from about a few minutes to one hour for dehydration. Otherwise, an imidation method may also be employed wherein a polyamic acid solution is cast on a glass plate or the like, followed by heating at a temperature of from 100 to 500° C. for about a few minutes to one hour for dehydration.

Further, it is also possible to employ a method wherein a dehydration catalyst such as a tertiary amine such as triethylamine, pyridine, isoquinoline, N,N-dimethylaminopyridine, and a dehydration agent such as an acid anhydride such as acetic anhydride, propionic anhydride or benzoic anhydride, as an imidation catalyst, are added and mixed to a polyamic acid solution, followed by casting on a glass plate or the like and then by heating usually at a temperature of from room temperature (about 20° C.) to 500° C. usually for from one hour to one full day for dehydration.

Further, an imidation method may also be employed wherein a polyamic acid solution is put into a large amount of a poor solvent to the polyamic acid, such as acetone, toluene, methanol or benzene for precipitation, and a powder obtained by filtration is heated and dried at a temperature of from 100 to 500° C. for from one hour to one full day. Further, an imidation method may also be employed wherein a polyamic acid solution is heated and dehydrated at a temperature of from room temperature (about 20° C.) to 200° C. for from one hour to one full day in an imidation catalyst comprising a dehydration catalyst such as a tertiary amine such as triethylamine, pyridine, isoquinoline, or N,N-dimethylaminopyridine, and a dehydration agent such as an acid anhydride such as acetic anhydride, propionic anhydride or benzoic anhydride, or in an organic solvent (an amido type solvent such as dimethylformamide or dimethylacetoamide) containing such an imidation catalyst.

The polyimide of the present invention has excellent characteristics such as high transparency with little coloration in addition to the high heat resistance, low dielectric constant, high dimensional stability, high mechanical strength and chemical resistance. Therefore, it is useful for various optical uses such as alignment films for liquid displays, optical waveguides or optical components. Further, it is useful for various applications in a field related to microelectronics, for example, as a material for high density electronic circuit boards, stress-relaxing films (buffer coating films) or surface protective films for semiconductor integrated circuits, protective films for various sensors or structural materials for optical waveguides, optical components of micromachines.

The entire disclosures of Japanese Patent Application No. 2004-134390 filed on Apr. 28, 2004, Japanese Patent Application No. 2004-134391 filed on Apr. 28, 2004 and Japanese Patent Application No. 2004-189465 filed on Jun. 28, 2004 including specifications, claims, drawings and summaries are incorporated herein by reference in their entireties.

EXAMPLES

Now, the present invention will be described in detail with reference to Examples, but it should be understood that the present invention is by no means restricted thereto. Further, in Examples, %, ppm and ppb are represented by "mass" unless otherwise specified.

Evaluation Methods

Moisture

Employing Micro Amount Moisture Measuring Device CA-100 Model, manufactured by Mitsubishi Chemical Corporation, 1 g of a sample was weighed and set in an anode cell of the device, whereupon the moisture value was measured.

BTC: Biphenyltetracarboxylic Acid

BTC in BPDA was analyzed by a high performance liquid chromatography (hereinafter LC) method. Prior to the measurement, the sample was esterified to determine the position of the peak in LC, followed by quantitative analysis.

Tri-Derivative

The tri-derivative in BPDA was analyzed by the LC method. Prior to the measurement, the sample was dissolved in an alkaline solution to determine the position of the peak in LC, followed by quantitative analysis.

Half-Derivative

The half-derivative in BPDA was analyzed by the LC method. Prior to the measurement, the sample was esterified to determine the position of the peak in LC, followed by quantitative analysis.

Light Transmittance

As an index for the degree of coloration of BPDA, the light transmittance of a solution of BPDA was measured. Specifically, a solution having the sample dissolved in a 2N NaOH aqueous solution at a concentration of 0.05 g/ml, was firstly prepared. Then, using a quartz cell having an inner diameter of 10 mm, and water as a contrast solution, the transmittance was measured by means of light with a wavelength of 400 nm by a spectrophotometer ("UV-265FW model", manufactured by Shimadzu Corporation). As NaOH, a guaranteed reagent was used, and as water for the preparation for a sample solution and for the contrast solution, distilled water or deionized water was used.

Pd

The Pd content was measured by inductively-coupled plasma mass spectrometry (ICP-MS). After adding 2 ml of sulfuric acid to 1 g of BPDA, decomposition was carried out in a dry system (with care to avoid burning, from 300° C., the temperature was gradually raised for carbonization, and ashing was completed at 600° C. over a period of 30 minutes), and hydrochloric acid was added to the obtained residue, and then hydrochloric acid was evaporated to dryness, followed by heat decomposition with nitric acid and volume adjustment to 25 ml to obtain a test sample, which was measured.

Example 1

Trade name Paddle Dryer NPD-1.6 W-G (effective volume: 65 L), manufactured by NARA MACHINERY CO., LTD., was used, as the heating device (1), as shown in FIGS. 1 to 4, which houses hollow rotary shafts (3) provided with a plurality of hollow rotary heating members (2) and which is designed to feed a heated heating medium to hollow portions (20) of the rotary heating members via hollow portions (30) of the rotary shafts, and also to a heating jacket (5), thereby to supply an amount of heat required for the reaction by heat transfer from each surface of such rotary shafts, rotary heating members and, if required, a heating jacket. In the heating device, the hollow rotary heating member (2) has a wedge shape as viewed from the side and a fan shape as viewed from the front and is secured at the neck portion of the fan shape to the rotary shaft (3).

To the above heating device, BTC (moisture: 18.31%) was continuously supplied from the inlet (41) for starting material at a rate of 7.8 kg/hr and subjected to a dehydration reaction for a retention time in the device of 7.3 hours under atmospheric pressure ($1.01325 \times 10^5$ Pa), and BPDA was continuously discharged from the outlet (42) for the product. In the obtained BPDA, the tri-derivative content was 0.036%, and the BTC residual amount was 0.004%. Further, at the time of the operation, nitrogen gas was introduced from the inlet (61) and discharged from the outlet (62) at a rate of 70 L/hr. Further, the amount of heat required for the reaction was supplied by adjusting the temperature and the flow rate of the heating medium, so that the prescribed operation conditions were attained.

The operation conditions of the device and the test results were as shown in the following Table.

TABLE 1

| Position | (Elapsed time) hr | Temperature of powder ° C. | BTC % | Tri-derivative % | Moisture % |
|---|---|---|---|---|---|
| Inlet | 0 | 20 | 100 | — | 18.31 |
| A | 0.5 | 110 | — | — | 0.71 |
| B | 1.0 | 176 | — | — | 0.082 |
| C | 2.7 | 248 | 0.045 | 0.054 | — |
| Outlet | 7.3 | 242 | 0.004 | 0.036 | — |

From the above Table, it is evident that the process for producing BPDA of the present invention has accomplished a conversion of 99.996% in a retention time of 7.3 hours and is thus excellent in productivity, and yet it has made it possible to maintain the high purity level with the content of the tri-derivative being 0.036%.

Example 2

Using the same device as in Example 1, heating of BTC was carried out by a continuous operation. From the starting material inlet (41) of the device, BTC (moisture: 18.31%) was continuously supplied at a rate of 7.4 kg/hr, and subjected to a dehydration reaction for a retention time in the device of 7.7 hours under atmospheric pressure, and from the outlet (42) for the product, BPDA was continuously discharged. At the time of the operation, nitrogen gas was introduced from the inlet (61) and discharged from the outlet (62) at a rate of 70 L/min. Further, the amount of heat required for the reaction was supplied by adjusting the temperature and the flow rate of the heating medium, so that the prescribed operation conditions were attained. The heating conditions of the starting material are shown in Table 2.

TABLE 2

| Temperature (° C.) | Time (hr) | Temperature-rising rate (° C./hr) |
|---|---|---|
| 20 → 110 | 0.5 | 180 |
| 110 → 176 | 0.5 | 132 |
| 176 → 210 | 0.6 | 57 |
| 210 → 248 | 1.1 | 35 |
| 248 | 5.0 | — |

Further, the time required for the temperature rise and the BTC temperatures at the respective portions in the device were measured, whereupon the temperature-rising rate was calculated. Namely, in this Example, in order to carry out the heating by a continuous method, the temperature was adjusted to have a distribution from the inlet to the outlet in the heating device, and the temperature of BTC was changed by moving BTC in the device. Accordingly, the temperature-rising rate of BTC is determined by the temperature distribution within the heating device and the moving speed of BTC. Namely, the operation was carried out at a temperature-rising rate of 180° C./hr from 20° C. to 110° C. at a rate of 57° C./hr from 176° C. to 210° C. and then at a rate of 35° C./hr from 210° C. to 248° C. Further, the temperature was maintained at 248° C. for 5 hours. Here, in each temperature range, the temperature-rising rate was constant. In the following Examples and Comparative Examples, the same is true unless otherwise specified. For example, when the temperature rise is initiated at 20° C., the temperature becomes 60° C. upon expiration of about 0.22 hour.

The temperature-rising time (the time for temperature rise from 60° C. to 210° C., the same applies hereinafter) was 1.38 hours, and during 1.38 hours i.e. at least ¼ of the temperature-rising time, the temperature-rising rate was higher than 50° C./hr. Further, the temperature was maintained to be from 150° C. to 250° C. for about 7 hours.

The obtained BPDA had a tri-derivative content of 0.05% and a half-derivative content of less than 0.1%, and the BTC residual amount was 0%. Further, the light transmittance of BPDA was 86%, and the Pd amount in the BPDA was 0.5 ppm.

Then, BPDA thus obtained, was transferred to a vertical evaporation oven equipped with a jacket and contacted with the surface of a drum type rotary cooler disposed at the forward end of a gas pipe directly connected to the gas phase portion of the evaporation oven at 305° C. under 203 Pa, and thereby cooled and precipitated (sublimation purification step). Crystals of BPDA deposited on the drum surface were continuously scraped by a scraping device and recovered as flakes.

Such flakes were pulverized, and BPDA thereby obtained had a tri-derivative content of 0.05% and a half-derivative content of less than 0.1%, and the BTC residual amount was 0%. Further, the light transmittance was 98% and the Pd amount was 0.7 ppb.

Example 3

Using the same device as in Example 1, the heating of BTC was carried out by a batch operation.

35 kg of BTC (moisture: 18.31%) was preliminarily charged to the device from the inlet (41) for starting material. The heating conditions of the starting material are shown in Table 3.

Here, the temperature rise of BTC was carried out by increasing the temperature of the heating medium to be supplied to the jacket (5), but during the temperature rise, BTC was not moved (the same is true in the following Examples and Comparative Examples, unless otherwise specified).

TABLE 3

| Temperature (° C.) | Example 3 | | Example 4 | | Example 5 | |
|---|---|---|---|---|---|---|
| | Time (hr) | Temperature-rising rate (° C./hr) | Time (hr) | Temperature-rising rate (° C./hr) | Time (hr) | Temperature-rising rate (° C./hr) |
| 60 → 100 | 0.5 | 80 | 2.0 | 20 | 0.5 | 80 |
| 100 → 180 | 0.5 | 160 | 0.5 | 160 | 0.5 | 160 |
| 180 → 230 | 0.5 | 100 | 0.5 | 100 | 2.0 | 25 |
| 230 | 7.0 | — | 7.0 | — | 7.0 | — |

Namely, the temperature was raised at a rate of 80° C./hr from 60° C. to 100° C., then at a rate of 160° C./hr from 100° C. to 180° C., and then, at a rate of from 100° C./hr, from 180° C. to 230° C., and further, the temperature was maintained at 230° C. for 7 hours for dehydration of BTC to form 25.5 kg of BPDA. The temperature-rising time was 1.3 hours, and during 1.3 hours i.e. at least ¼ of the temperature-rising time, the temperature-rising rate was higher than 50° C./hr. Further, the temperature was maintained from 150° C. to 250° C. for about 7.7 hours. Further, at the time of the operation, nitrogen gas was introduced from the inlet (61) and discharged from the outlet (62) at a rate of 20 L/min.

The obtained BPDA had a tri-derivative content of 0.05% and a half-derivative content of less than 0.1%, and the residual amount of BTC was 0%. Further, the light transmittance of BPDA was 91%, and the amount of Pd in BPDA was 0.5 ppm.

Then, BPDA thus obtained was subjected to sublimation purification in the same manner as in Example 2, whereby crystals of BPDA were recovered as flakes. The flakes were pulverized, and the obtained BPDA had a tri-derivative content of 0.05% and a half-derivative content of less than 0.1%, and the residual amount of BTC was 0%. Further, the light transmittance was 99%, and the amount of Pd was 0.3 ppb.

Example 4

The heating and sublimation purification were carried out under the same conditions as in Example 3 except that the heating conditions were changed as shown in Table 3. The temperature-rising time was 2.8 hours, and during 0.8 hour i.e. at least ¼ of the temperature-rising time, the temperature-rising rate was higher than 50° C./hr. Further, the temperature was maintained at from 150° C. to 250° C. for about 7.7 hours.

Example 5

The heating and sublimation purification were carried out under the same conditions as in Example 3 except that the heating conditions were changed as shown in Table 3. The temperature-rising time was 2.2 hours, and during 1.0 hour i.e. at least ¼ of the temperature-rising time, the temperature-rising rate was higher than 50° C./hr. Further, the temperature was maintained at from 150° C. to 250° C. for about 9.2 hours.

Example 6

The heating and sublimation purification were carried out under the same conditions as in Example 3 except that the heating conditions were changed as shown in Table 4.

TABLE 4

| Temperature (° C.) | Time (hr) | Temperature-rising rate (° C./hr) |
|---|---|---|
| 60 → 100 | 0.5 | 80 |
| 100 → 180 | 0.5 | 160 |
| 180 → 245 | 0.5 | 130 |
| 245 | 5.0 | — |

The temperature-rising time was 1.23 hours, and during 1.23 hours i.e. at least ¼ of the temperature-rising time, the temperature-rising rate was higher than 50° C./hr. Further, the temperature was maintained from 150° C. to 250° C. for about 5.7 hours.

Comparative Example 1

Using a device which was different from the device in Example 1 in that the shape of hollow rotary heating members in the heating device was a disk-shape, the heating of BTC was carried out by a batch operation.

35 kg of BTC (moisture 18.31%) was preliminarily charged to the device from the inlet (41) for starting material. The heating conditions of the starting material are shown in Table 5.

TABLE 5

| Temperature (° C.) | Time (hr) | Temperature-rising rate (° C./hr) |
| --- | --- | --- |
| 80 → 100 | 0.7 | 30 |
| 100 | 1.0 | — |
| 100 → 130 | 1.2 | 25 |
| 130 | 2.0 | — |
| 130 → 280 | 4.3 | 35 |
| 280 | 20.0 | — |

Namely, the temperature rise was carried out at a rate of 30° C./hr from 80° C. to 100° C., then the temperature was maintained at 100° C. for one hour, and then the temperature-rise was carried out at a rate of 25° C./hr from 100° C. to 130° C. Then, the temperature was maintained at 130° C. for two hours, and further, the temperature-rise was carried out at a rate of 35° C./hr from 130° C. to 280° C., and then the temperature was maintained at 280° C. for 20 hours, to form 25.5 kg of BPDA. In the temperature-rising time, there was no time when the temperature-rising rate was higher than 50° C./hr. Further, at the time of the operation, nitrogen gas was introduced from the inlet (61) and discharged from the outlet (62) at a rate of 20 L/min.

The obtained BPDA had a tri-derivative content of 0.06% and a half-derivative content of not more than 0.1%, and the residual amount of BTC was 0%. Further, the light transmittance of BPDA was 59%, and the amount of Pd in BPDA was 0.5 ppm.

Then, BPDA thus obtained was subjected to sublimation purification in the same manner as in Example 2, and crystals of BPDA were recovered as flakes. Such flakes were pulverized, and the obtained BPDA had a tri-derivative content of 0.06%, and a half-derivative content of less than 0.1%, and the residual amount of BTC was 0%. Further, the light transmittance was 89%, and the amount of Pd was 2 ppb.

The results of evaluation of BPDA obtained in the above Examples 2 to 6 and Comparative Example 1 are shown in Table 6.

TABLE 6

| | | Example 2 | Example 3 | Example 4 | Example 5 | Example 6 | Comparative Example 1 |
| --- | --- | --- | --- | --- | --- | --- | --- |
| Before sublimation purification | BTC | 0 | 0 | 0 | 0 | 0 | 0 |
| | Tri-derivative (%) | 0.05 | 0.05 | 0.05 | 0.05 | 0.05 | 0.06 |
| | Half-derivative (%) | 0.1> | 0.1> | 0.1> | 0.1> | 0.1> | 0.1> |
| | Light transmittance (%) | 86 | 91 | 91 | 90 | 87 | 59 |
| | Amount of Pd (ppm) | 0.5 | 0.5 | 0.5 | 0.5 | 0.5 | 0.5 |
| After sublimation purification | BTC | 0 | 0 | 0 | 0 | 0 | 0 |
| | Tri-derivative (%) | 0.05 | 0.05 | 0.05 | 0.05 | 0.05 | 0.06 |
| | Half-derivative (%) | 0.1> | 0.1> | 0.1> | 0.1> | 0.1> | 0.1> |
| | Light transmittance (%) | 98 | 99 | 98 | 98 | 98 | 89 |
| | Amount of Pd (ppb) | 0.7 | 0.3 | 0.3 | 0.4 | 0.7 | 2 |

BPDA after the sublimation purification obtained in each of Examples 2 to 6 had a light transmittance of at least 98% and thus had an extremely low degree of coloration, and further, the amount of Pd was extremely small at a level of from 0.3 to 0.7 ppb, thus indicating high quality BPDA with high purity.

Example 7

Preparation of Polyimide Film

Into a 500 ml reactor equipped with a stirrer and heater, 9.66 g of 4,4'-diaminodiphenylether (hereafter referred to as DDE) and 175.0 g of N-methylpyrrolidone (hereinafter referred to as NMP) were charged to obtain a homogeneous solution. Then, 14.20 g of BPDA crystals after the sublimation purification obtained in Example 3 were added thereto, followed by a reaction with stirring at a temperature of 25° C. for 24 hours to obtain a viscous polyamic acid solution. The obtained solution was diluted with NMP to obtain a solution having a viscosity of 300 poise, which was cast on a glass plate and stepwisely heated from 100° C. to 300° C. in a hot air dryer, to obtain a polyimide film having a thickness of 11 μm. The light transmittance at 400 nm of the obtained polyimide film was measured by a spectrophotometer ("UV-265FW model" manufactured by Shimadzu Corporation) and found to be 30%.

Comparative Example 2

A polyimide film was obtained in the same manner as in Example 7 except that as BPDA, BPDA before the sublimation purification in Comparative Example 1 was used. The light transmittance at 400 nm of the obtained polyimide film was 7%.

INDUSTRIAL APPLICABILITY

BPDA of the present invention has high purity and is excellent in the polymerization degree of an aromatic polyimide, and thus, it is widely useful for application to highly functional gas separation films or flexible printed circuit boards and for various other applications.

The invention claimed is:

1. A biphenyltetracarboxylic acid dianhydride, wherein a solution obtained by dissolving the dianhydride at a concentration of 0.05 g/ml in a 2N NaOH aqueous solution has a transmittance of light with a wavelength of 400 nm of at least 98%.

2. The dianhydride of claim 1, which has a palladium content of not higher than 0.2 mass ppm.

3. A biphenyltetracarboxylic acid dianhydride, wherein a solution obtained by dissolving the dianhydride at a concentration of 0.05 g/ml in a 2N NaOH aqueous solution has a transmittance of light with a wavelength of 400 nm of at least 98%, obtained by heating and sublimation purification of biphenyltetracarboxylic acid, wherein the heating is carried out at a pressure of from $1 \times 10^2$ Pa to $1.1 \times 10^5$ Pa to a maximum temperature in a range of from 210° C. to 250° C. in such a manner that a rate of temperature increase is higher than 50° C./hr for a period of at least ¼ of the time for a temperature rise from 60° C. to 210° C., and the temperature is maintained to be from 150° C. to 250° C. for from 0.5 to 10 hours.

4. The dianhydride of claim 1, produced by a process comprising:

heating biphenyltetracarboxylic acid to produce biphenyltetracarboxylic acid dianhydride, wherein the heating is carried out with a heating device which comprises, housed therein, a hollow rotary shaft comprising a plurality of hollow rotary heating members and which is designed to feed a heated heating medium to hollow portions of the rotary heating members via a hollow portion of the rotary shaft, to thereby supply an amount of heat required for reaction by heat transfer from each surface of the rotary shaft, rotary heating members, wherein each of the hollow rotary heating members has a wedge shape as viewed from a side and a fan shape as viewed from a front and is secured at a neck portion of the fan shape to the hollow rotary shaft, and wherein a biphenyltetracarboxylic acid powder is continuously supplied from a first end of the heating device as a starting material, wherein the powder is heated as it is contacted with the hollow rotary heating members which are rotating, wherein the powder is subjected to a dehydration reaction while it is transferred in an axial direction in the heating device, and wherein biphenyltetracarboxylic acid dianhydride is continuously discharged as a product from a second end of the heating device.

5. The dianhydride of claim 4, wherein, in the heating device, at least two such hollow rotary shafts are provided in a horizontal direction in parallel to one another; on each rotary shaft, rotary heating members disposed at two positions symmetrical about a point, as viewed from the front, are provided alternately in the axial direction in a predetermined number at equal distances; and the groups of rotary heating members provided on the adjacent rotary shafts take such spatial disposition that they are mutually free from contact with each other during rotation of both rotary shafts.

6. The dianhydride of claim 5, wherein the heating device further comprises a heating jacket, wherein the hollow rotary shaft is also designed to feed a heated heating medium to a hollow portion of the heating jacket via a hollow portion of the rotary shaft, and wherein to the amount of heat required for the reaction is also supplied by heat transfer from each surface of the heating jacket.

7. The dianhydride of claim 4, wherein the heating is followed by sublimation purification.

8. The dianhydride of claim 4, wherein the sublimation purification is carried out at a temperature of at least 250° C.

9. The dianhydride of claim 3, wherein the dianhydride obtained by the process is 3,4,3',4'-biphenyltetracarboxylic acid dianhydride.

* * * * *